US00PP08435P

United States Patent [19]

Noodelijk

[11] Patent Number: Plant 8,435

[45] Date of Patent: Oct. 26, 1993

[54] CHRYSANTHEMUM NAMED RESPECTFUL

[75] Inventor: Rob Noodelijk, Woubrugge, Netherlands

[73] Assignee: Chrysanthemum Breeders Association, N.V., Netherlands Antilles

[21] Appl. No.: 785,823

[22] Filed: Oct. 31, 1991

[51] Int. Cl.[5] ..... A01H 5/00

[52] U.S. Cl. ..... Plt./82.1

[58] Field of Search ..... Plt./82.1, 82.2

[56] References Cited

U.S. PATENT DOCUMENTS

P.P. 5,477 5/1985 van Veen ..... Plt. 82.1

*Primary Examiner*—Howard J. Locker

*Attorney, Agent, or Firm*—Parkhurst, Wendel & Rossi

[57] ABSTRACT

A new and distinct cultivar of Chrysanthemum plant named Respectful, bearing large sized white blooms with a yellow green center and a performance of 14–16 days.

2 Drawing Sheets

ORIGIN AND HISTORY OF THE NEW PLANT

The new plant of the present invention comprises a new and distinct cultivar of Chrysanthemum plant which is a cross of a Chrysanthemum morifolium plant named Refour U.S. Plant Pat. No. 5,477) and a male parent of *Chrysanthemum morifolium* named 'Delta' (U.S. Plant Pat. No. 5,815). The invention was discovered by Rob Noodelijk, Vrouwgeestweg 26, 2481 KN Woubrugge, Holland in a greenhouse in 1988. The invention has been asexually reproduced by cuttings at Ter Aar, Holland. The new cultivar has been found to retain its distinctive characteristics through successive propagations.

SUMMARY OF THE NEW PLANT

The present invention is a new and distinct variety of Chrysanthemum of a large sized bloom and white color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the full bloom of the new cultivar.

Sheet 2, top, shows various stages of bloom of the new cultivar; and

Sheet 2, bottom, shows the foliage and petiole of the new cultivar.

DESCRIPTION OF THE INVENTION

This new variety of Chrysanthemum is of the botanical classification *Chrysanthemum morifolium*, and is named Respectful. When grown in the vicinity of Ter Aar, Holland, it has a response time of approximately 8 weeks. This new variety produces large sized white blooms with a yellow green center having a 2½ week performance (i.e., vase life between 14–16 days). This new variety of Chrysanthemum has been found to retain its distinctive characteristics throughout successive propagations and may be planted under greenhouse conditions in Holland between weeks fifty and thirty-five (December 1 and August 30).

The following is a description of the plant and characteristics (color designations from R.H.S. Color Chart)

that distinguish it over related known varieties and its antecedents:

Botanical classification: *Chrysanthemum morifolium.*

Bud:

*Size.*—Large cross section ±1.2 cm, height ±0.9 cm.

*Form.*—Round and flat.

*Outside color.*—White 155D.

Bloom:

*Size.*—Large.

*Fully expanded.*—8–9 cm.

*Borne.*—Single.

*Stems.*—Strong, thin.

*Forms.*—Single.

*Performance.*—Normal, 14–16 Days (18° C.–20° C.).

*Center of flower.*—Immature: Yellow Green 153 A. Mature: Yellow Orange 153 B to 153 C.

*Base of petals.*—White 155D.

*Inside of petals.*—White 155D.

*Reverse of petals.*—White 155D.

*Outer Petals.*—White 155D.

*Tonality from a distance.*—A white daisy with a dark green center and a lot of petals.

*Discoloration.*—None.

*Pollen.*—Yellow-orange 14A.

Petals:

*Texture.*—Upperside rough, underside smooth.

*Number.*—42–48 (two-three rows).

*Cross-section.*—Flat, two keels.

*Arrangements.*—Imbricated.

*Persistence.*—Good, Petals keep straight or reflex somewhat at the edge at the end of blooming.

*Fragrance.*—Typical Chrysanthemum.

Reproductive organs:

*Stamen.*—Yellow green, thin and ±5 mm in length.

*Pollen.*—Appears at a late stage of blooming.

*Styles.*—Green, thin.

*Length.*—±6 mm.

*Stigmas.*—Yellow green.

*Width.*—±2 mm.

*Ovaries.*—Enclosed in calyx.

Plant:

*Form.*—Spray mum meant for erect culture herbaceous.

*Growth.*—Strong.

*Height.*—110-135 cm.

*Peduncle.*—Near the top ±16 cm, near the middle ±27 cm, near the bottom ±30 cm.

*Internodes.*—±3½ cm.

*Flowering response.*—8 weeks.

Foliage:

*Color.*—Upperside green 136A, underside green 136B.

*Size.*—Length ±11 cm, width ±8 cm.

*Quantity.*—22-28.

*Shape.*—Lobed. See photograph.

*Texture.*—Upperside rough, underside smooth, slightly hirsute.

*Ribs and Veins.*—Ribs and veins well developed.

*Edge.*—Crenated.

What is claimed is:

1. A new and distinct cultivar of Chrysanthemum named Respectful as described and illustrated.

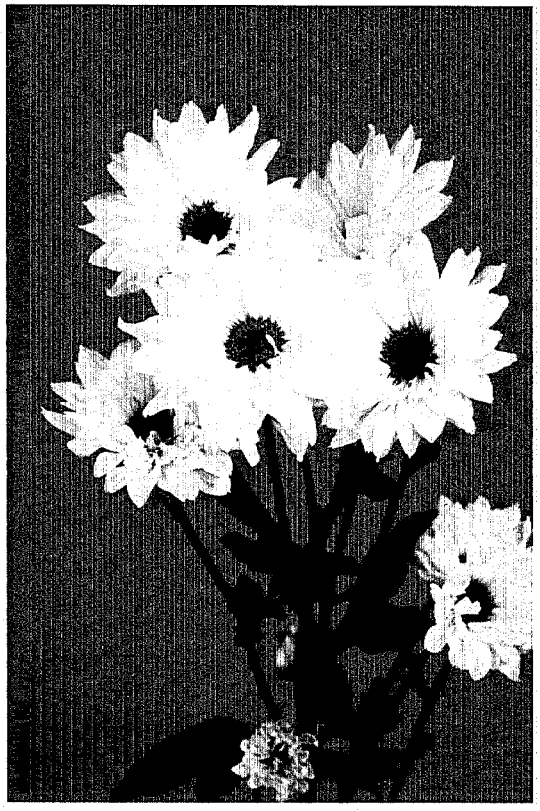

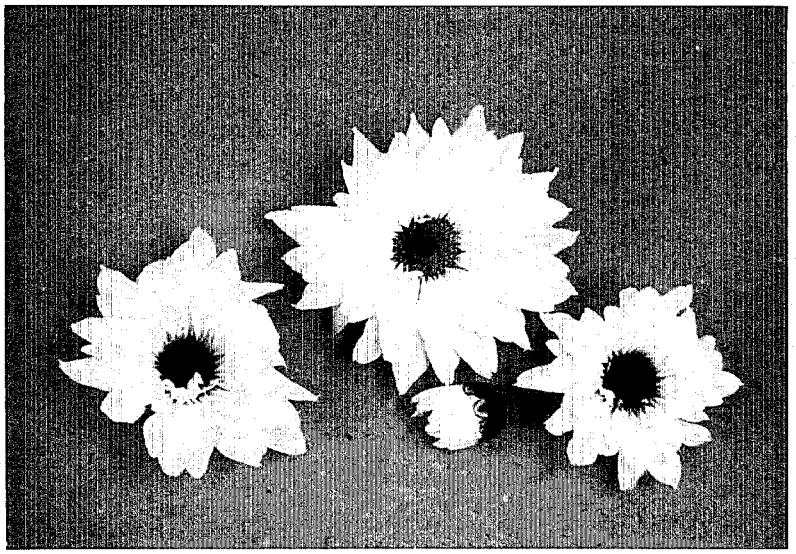
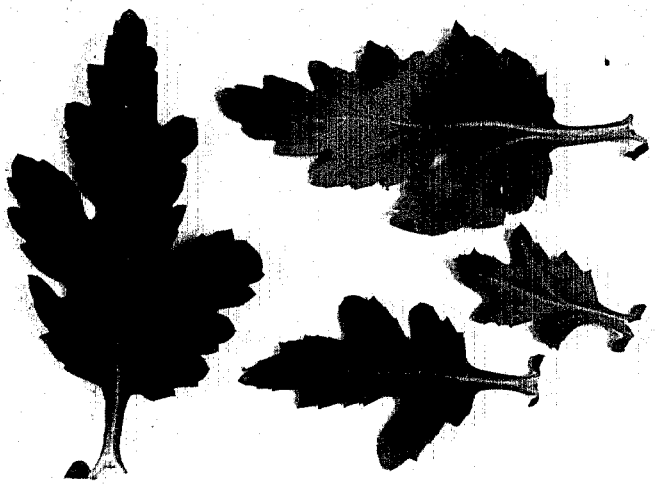

* * * * *